United States Patent [19]

Hassall et al.

[11] 4,046,751
[45] Sept. 6, 1977

[54] SUBSTITUTED PHENYL KETONES

[75] Inventors: Cedric Herbert Hassall, Welwyn; William Henry Johnson, Hitchin; Antonin Krohn, London; Carey Ernest Smithen, Welwyn; William Anthony Thomas, Huntingdon, all of England

[73] Assignee: Hoffmann-La Roche Inc., Nutley, N.J.

[21] Appl. No.: 741,084

[22] Filed: Nov. 11, 1976

Related U.S. Application Data

[62] Division of Ser. No. 605,580, Aug. 18, 1975, Pat. No. 4,007,219.

[30] Foreign Application Priority Data

Aug. 20, 1974 United Kingdom ............... 36567/74
May 21, 1975 United Kingdom ............... 21821/75
Aug. 11, 1975 United Kingdom ............... 36567/75

[51] Int. Cl.$^2$ .................... C07D 213/51; A61K 31/44
[52] U.S. Cl. .................... 260/112.5 R; 260/295 AM; 424/263
[58] Field of Search ................. 260/295 AM, 112.5 R

[56] References Cited

U.S. PATENT DOCUMENTS 3,534,031 10/1970 Bell et al. .............................. 260/244

Primary Examiner—James O. Thomas, Jr.
Assistant Examiner—Lisa Jones
Attorney, Agent, or Firm—Samuel L. Welt; George M. Gould; Frank P. Hoffman

[57] ABSTRACT

This invention is directed toward pharmacologically active compounds of the formula

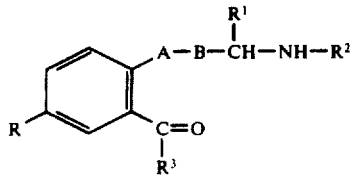

wherein A represents a nitrogen atom which may be substituted by a methyl, cyclopropylmethyl, di(C$_{1-4}$alkyl)aminoethyl, methoxymethyl or hydroxyethyl group and B represents a carbonyl group or A and B together represent a grouping of the formula

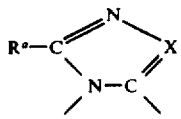

in which R$^a$ represents a hydrogen atom or a lower alkyl or hydroxymethyl group and X represents a nitrogen atom or C-R$^b$ wherein R$^b$ represents a hydrogen atom or a lower alkyl or hydroxymethyl group; R represents a halogen atom or a nitro or trifluoromethyl group; R$^1$ represents a hydrogen atom or a lower alkyl group; R$^2$ represents an acyl group derived from a naturally occurring amino acid (all such groups which contain an asymmetric carbon atom having the L- or D,L-configuration) and R$^3$ represents a phenyl, halophenyl or 2-pyridyl group and acid addition salts thereof.

Also provided are methods for their preparation and intermediates thereof. These compounds exhibit activity as anticonvulsants, muscle relaxants and sedatives.

1 Claim, No Drawings

SUBSTITUTED PHENYL KETONES

This is a division of application Ser. No. 605,580 1 filed Aug. 18, 1975, now U.S. Pat. No. 4,007,219.

DESCRIPTION OF THE INVENTION

The present invention is concerned with substituted phenyl ketones and a process for the manufacture thereof.

The substituted phenyl ketones provided by the present invention are compounds of the general formula

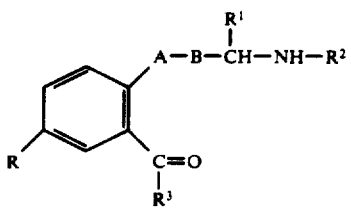

wherein A represents a nitrogen atom which may be substituted by a methyl, cyclopropylmethyl, di($C_{1-4}$alkyl)mainoethyl, methoxymethyl or hydroxyethyl group and B represents a carbonyl group or A and B together represent a grouping of the formula

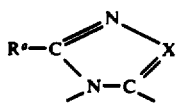

in which $R^a$ represents a hydrogen atom or a lower alkyl or hydroxymethyl group and X represents a nitrogen atom or C—$R^b$ wherein $R^b$ represents a hydrogen atom or a lower alkyl or hydroxymethyl group; R represents a halogen atom or a nitro or trifluoromethyl group; $R^1$ represents a hydrogen atom or a lower alkyl group; $R^2$ represents an acyl group derived from a naturally occurring amino acid (all such groups which contain an asymmetric carbon atom having the L- or D,L-configuration) and $R^3$ represents a phenyl, halophenyl or 2-pyridyl group and acid addition salts thereof.

It will be appreciated that formula I hereinbefore embraces compounds of the general formulae

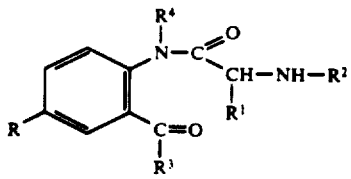

and

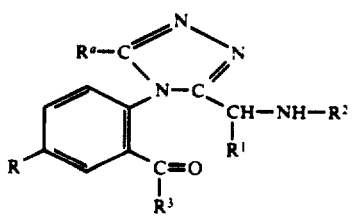

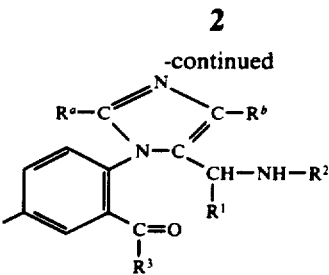

wherein R, $R^1$, $R^2$, $R^3$, $R^a$ and $R^b$ have the significance given earlier and $R^4$ represents a hydrogen atom or a methyl, cyclopropylmethyl, di($C_{1-4}$alkyl)aminoethyl, methoxymethyl or hydroxyethyl group.

As used in this specification, the term "lower alkyl" means a straight-chain or branched-chain alkyl group which preferably contains from 1 to 6 carbon atoms (e.g., methyl, ethyl, propyl, isopropyl, butyl, hexyl and the like). The methyl group is the preferred lower alkyl group. The term "halogen" means fluorine, chlorine, bromine or iodine. The acyl group denoted by $R^2$ is preferably derived from a naturally occurring alpha-amino carboxylic acid such as glycine or L- or D,L-alanine, -leucine, -phenylalanine, -isoleucine, -serine, -lysine, -methionine, -proline and the like. Especially preferred acyl groups are those derived from L-amino acids, particularly from L-phenylalanine or L-lysine. The preferred halogen value for R is chlorine or bromine when $R^3$ represents a phenyl or halophenyl group and bromine when $R^3$ represents a 2-pyridyl group. The halophenyl group denoted by $R^3$ includes a monohalophenyl group, especially an O-halophenyl group such as o-chlorophenyl or o-fluorophenyl, and a dihalophenyl group, especially an o,o'-dihalophenyl group such as o,o'-dichlorophenyl.

Preferred compounds of formula Ia hereinbefore are those in which R represents a chlorine or bromine atom or a nitro group, $R^1$ represents a hydrogen atom, $R^3$ represents a phenyl, o-fluorophenyl, o-chlorophenyl or 2-pyridyl group and $R^4$ represents a hydrogen atom or a methyl, diethylaminoethyl or methoxymethyl group.

Examples of compounds of formula Ia hereinbefore are:

L-phenylalanyl-N-(4-bromo-2-picolinoylphenyl)-glycinamide,
glycyl-N-(4-bromo-2-picolinoylphenyl)glycinamide,
L-leucyl-N-(b 4-bromo-2-picolinoylphenyl)glycinamide,
L-lysyl-N-(4-bromo-2-picolinoylphenyl)glycinamide,
L-isoleucyl-N-(4-bromo-2-picolinoylphenyl)glycinamide,
L-gamma-glutamyl-N-(4-bromo-2-picolinoylphenyl)-glycinamide,
L-alanyl-N-(4-bromo-2-picolinoylphenyl)glycinamide,
L-arginyl-N-(4-bromo-2-picolinoylphenyl)glycinamide,
L-alpha-glutamyl-N-(4-bromo-2-picolinoylphenyl)-glycinamide,
glycyl-N-(2-benzoyl-4-chlorophenyl)glycinamide,
glycyl-N-(2-benzoyl-4-nitrophenyl)glycinamide,
L-prolyl-N-(2-benzoyl-4-nitrophenyl)glycinamide,
glycyl-N-(2-benzoyl-4-chlorophenyl)-N-methyl-glycinamide,
L-alanyl-N-(2-benzoyl-4-chlorophenyl)-N-methyl-glycinamide, L-phenylalanyl-N-(2-benzoyl-4-chlorophenyl)-N-methylglycinamide, L-lysyl-N-(2-benzoyl-4-chlorophenyl)-N-methylglycinamide and L-leucyl-N-(2-benzoyl-4-chlorophenyl)-N-methylglycinamide, L-phenylalanyl-N-(2-benzoyl-4-nitrophenyl)glycinamide, L-arginyl-N-(2-benzoyl-4-chlorophenyl)glycinamide, L-alanyl-N-(2-benzoyl-4-nitrophenyl)glycinamide, L-alanyl-N-[2-(2'-fluorobenzoyl)-4-nitrophenyl]-N-methylglycinamide and L-phenylalanyl-N-(2-benzoyl-4-chlorohenyl)-N-methyl-L-alaninamide.

Preferred compounds of formula Ib hereinbefore are those in which R represents a chlorine atom, $R^1$ represents a hydrogen atom, $R^3$ represents a phenyl or o-chlorophenyl group and $R^a$ represents a methyl or hydroxymethyl group.

Examples of compounds of formula Ib are:

5-chloro-2-[3-(L-phenylalanylaminomethyl)-5-methyl-4H-1,2,4-triazol-4-yl]benzophenone, 5-chloro-2-[3-(L-lysylaminomethyl)-5-methyl-4H-1,2,4-triazol-4-yl]benzophenone, 2',5-dichloro-2-[3-(L-phenylalanylaminomethyl)-5-methyl-4H-1,2,4-triazol-4-yl]benzophenone, 2'5-dichloro-2-[3-(L-lysylaminomethyl)-5-methyl-4H-1,2,4-triazol-4-yl]benzophenone and 2'5-dichloro-2-(3-glycylaminomethyl-5-methyl-4H-1,2,4-triazol-4-yl)benzophenone.

Preferred compounds of formula Ic hereinbefore are those in which R represents a chlorine atom, $R^1$ represents a hydrogen atom, $R^3$ represents a phenyl or o-fluorophenyl group, $R^a$ represents a methyl or hydroxymethyl group and $R^b$ represents a hydrogen atom.

Examples of compounds of formula Ic are:

5-chloro-2'-fluoro-2-[5-(L-leucylaminomethyl)-2-methyl-1-imidazolyl] benzophenone and 5-chloro-2'-fluoro-2-[5-(l-alanylaminomethyl)-2-methyl-1-imidazolyl] benzophenone.

According to the process provided by the present invention, the substituted phenyl ketones aforesaid (i.e., the compounds of formula I hereinbefore and their acid addition salts) are manufactured by a. cleaving off in accordance with methods known per se the protecting group or protecting groups present in the group $R^{20}$ in a compound of the general formula

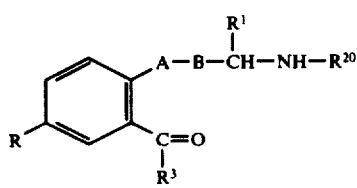

II wherein A, B, R, $R^1$ and $R^3$ have the significance given earlier and $R^{20}$ represents the acyl group of a naturally occurring amino acid in which the amino groups or amino groups present is/are in protected form and any other functional group which may be present is in protected form where required (all such acyl groups which contain an asymmetric carbon atom having the L- or D,L-configuration) or b. resolving a racemate of formula I hereinbefore into its optical isomers and isolating the L-isomer or c. for the manufacture of a compound of formula I in which A represents a nitrogen atom which may be substituted by a methyl, cyclopropylmethyl, di($C_{1-4}$alkyl)aminoethyl, methoxymethyl or hydroxyethyl group and B represents a carbonyl group, R represents a nitro group and $R^2$ represents an acyl group derived from a naturally occurring amino acid which is not affected by nitrating agents (all such groups which contain an asymmetric carbon atom having the L- or D,L-configuration), nitrating a compound of the general formula

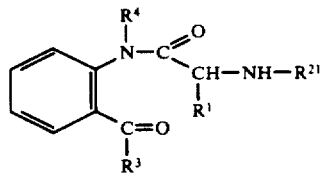

wherein $R^1$, $R^3$ and $R^4$ have the significance given earlier and $R^{21}$ represents an acyl group derived from a naturally occurring amino acid which is not affected by nitrating agents (all such groups which contain an asymmetric carbon atom having the L- or D,L-configuration) and, if desired, converting a free base obtained into an acid addition salt or converting an acid addition salt obtained into a free base or into a different acid addition salt.

The amino group or amino groups present in the acyl group denoted by $R^{20}$ in formula II can be protected with any amino protecting group which is well known in peptide chemistry. Especially suitable amino protecting groups for the purpose of the present invention are aralkoxycarbonyl groups, particularly the benzyloxycarbonyl groups, and the tertbutoxycarbonyl group. The amino protecting group may also be a formyl, trityl or trifluoroacetyl group. Any carboxy or hydroxy group which may be present in the acyl group denoted by $R^{20}$ in formula II can be protected by a conventional carboxy protecting or hydroxy protecting group respectively. For example, a carboxy group may be protected by conversion into an alkyl ester (e.g., a tertbutyl ester) or an aralkyl ester (e.g., a benzyl ester). Again, for example, a hydroxy group may be protected, for example, by means of an aralkoxycarbonyl group (e.g., benzyloxycarbonyl), an alkanoyl group (e.g., acetyl, propionyl, etc.), an aroyl group (e.g., benzoyl), an alkyl group (e.g., tertbutyl) or an aralkyl group (e.g., benzyl). The protection of other functional groups present in the acyl group denoted by $R^{20}$ may be carried out in a known manner.

The removal of the protecting group or protecting groups present in the acyl group denoted by $R^{20}$ in a compound of formula II is carried out in accordance with methods known per se; that is to say, methods in actual use for or described in the literature on the removal of protecting groups. In a preferred embodiment of the present process, the acyl group denoted by $R^{20}$ carries a protecting group of protecting groups which are removable by hydrolysis. Thus, for example, an aralkoxycarbonyl group (e.g., benzyloxycarbonyl) or a tertbutoxycarbonyl group may be removed by treatment with a mixture of hydrogen bromide and acetic acid. The tertbutoxycarbonyl group may also be removed by means of hydrogen chloride in an organic solvent (e.g., dioxan) or by means of trifluoroacetic acid. A benzyloxycarbonyl or a tertbutoxycarbonyl group may also be removed by treatment with boron trichloride or boron tribromide in an inert organic solvent such as dichloromethane.

A racemate of formula I hereinbefore can be split up into its optical isomers in accordance with known methods; for example, with the aid of an appropriate optically active acid. The desired L-isomer can be obtained according to known methods such as fractional crystallization of the diastereoisomeric salts obtained.

The nitration of a compound of formula II hereinbefore can be carried out according to methods known per se. For example, the nitration can be carried out using an alkali metal nitrate, preferably potassium nitrate, in the presence of a strong mineral acid, preferably anhydrous sulfuric acid, or a strong organic acid, preferably anhydrous trifluoroacetic acid. The acyl group denoted by $R^{21}$ in the compounds of formula III is preferably derived from glycine or L- or D,L-alanine, valine, leucine, isoleucine, lysine, proline or aspartic acid.

The starting materials of formula II hereinbefore can be prepared by a variety of routes.

Thus, starting materials of formula II can be prepared, for example, by condensing an amine of the general formula

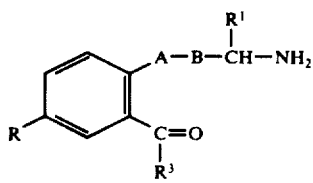

IV wherein A, B, R, $R^1$ and $R^3$ have the significance given earlier with an appropriately protected amino acid or a reactive derivative thereof.

The condensation can be carried out in accordance with methods which are known per se in peptide chemistry; for example, by the mixed anhydride, azide, activated ester or acid chlorine method.

In one method, an appropriate amine of formula IV can be condensed with an appropriately protected amino and in which the terminal carboxy function is a mixed anhydride residue formed with an organic or inorganic acid. Suitably, such an amino acid carrying a free carboxy function is treated with a tertiary base such as a tri)lower alkyl)amine (e.g., triethylamine) or N-ethylmorpholine in an inert organic solvent (e.g., tetrahydrofuran, dichloromethane or 1,2-dimethoxyethane) and the resulting salt is reacted with a chloroformic acid ester (e.g., the ethyl or isobutyl ester) at a lower temperature. The mixed anhydride obtained is then suitably condensed in situ with the amine of formula IV.

In another method, an appropriate amine of formula IV can be condensed with an appropriately protected amino acid in which the terminal carboxy group is in the form of an acid azide. This condensation is preferably carried out in an inert organic solvent such as dimethylformamide or ethyl acetate at a low temperature.

In yet another method, an appropriate amine of formula IV can be condensed with an appropriately protected amino acid in which the terminal carboxy function is in the form of an active ester group (e.g., the p-nitrophenyl, 2,4,5-trichlorophenyl or N-hydroxysuccinimide ester group). This condensation is suitably carried out at about $-20°$ C. in an inert organic solvent such as dimethylformamide.

In a further method, an appropriate amine of formula IV can be condensed with an appropriately protected amino acid in which the terminal carboxy function is in the form of an acid chloride. This condensation is preferably carried out in the presence of a base and at a low temperature.

Alternatively, starting materials of formula II in which A represents a nitrogen atom which may be substituted by a methyl, cyclopropylmethyl, di($C_{1-4}$alkyl)aminoethyl, methoxymethyl or hydroxyethyl group and B represents a carbonyl group can be prepared by condensing a compound of the general formula

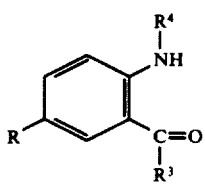

V wherein R, $R^3$ and $R^4$ have the significance given earlier with an appropriately protected dipeptide or a reactive derivative thereof using one of the methods hereinbefore in connection with the condensation of an amine of formula IV with a protected amino acid or a reactive derivative thereof.

The amines of formula IV hereinbefore in which A represents a nitrogen atom which may be substituted by a methyl, cyclopropylmethyl, di($C_{1-4}$alkyl) aminoethyl, methoxymethyl or hydroxyethyl group and B represents a carbonyl group can be obtained, for example, by condensing a compound of formula V hereinbefore with an appropriately protected amino acid or a reactive derivative thereof followed by removal of the protected group in the manner previously described.

Alternatively, the amines of formula IV in which A represents a nitrogen atom which is substituted by a di($C_{1-4}$alkyl)aminoethyl group and B represents a carbonyl group and/or $R^3$ represents a 2-pyridyl group or in which A and B together represent a grouping of formula (i) hereinbefore can be obtained by hydrolyzing a 1,4-benzodiazepine of the general formula

VI wherein A', B', R,$R^1$ and $R^{30}$ have any of the values accorded to A, B, R, $R^1$ and $R^3$ hereinbefore with the proviso that when A' represents a nitrogen atom which may be substituted by a methyl, cyclopropylmethyl, methoxymethyl or hydroxyethyl group and B represents a carbonyl group, then $R^{30}$ represents a 2-pyridyl group with a mineral acid. Thus, a 1,4-benzodiazepine of formula VI can be hydrolyzed with sulfuric acid, nitric acid, phosphoric acid or, preferably, a hydrohalic acid such as hydrochloric acid. The hydrolysis is preferably carried out at a temperature of ca $20°-30°$ C.

The 1,4-benzodiazepines of formula VI hereinbefore in which A' and B' together represent a grouping of formula (i) wherein X represents C-R$^b$ do not form part of the present invention, but their preparation is described herein for sake of completeness. They may be prepared, for example, by the nitrosation of a compound of the general formula

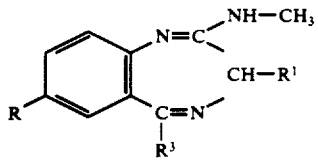
VII wherein R, R$^1$ and R$^3$ have the significance given earlier to give a compound of the general formula

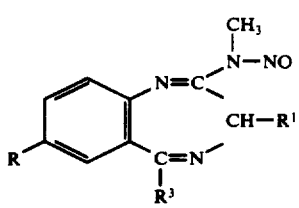
VIII wherein R, R$^1$ and R$^3$ have the significance given earlier.

This nitrosation may be carried out using nitrous acid which is formed in situ. Reagents which may be used for this purpose include alkali metal nitrites (e.g., sodium nitrite) in the presence of an inorganic or organic acid (e.g., glacial acetic acid) and an aqueous or non-aqueous solvent, alkyl nitrites (e.g., methyl nitrite) in the presence of an inert solvent such as an alkanol, a chlorinated hydrocarbon or dimethylformamide, and a solution of nitrosyl chloride gas in inert solvent and in the presence of an acid acceptor (e.g., pyridine). Such a nitrosation should be carried out at a temperature below room temperature (e.g., a temperature in the range of −20° to 25° C.).

It will be appreciated that the grouping —N(CH$_3$)(NO) in the 2-position of a compound of formula VIII is a leaving group and that equivalent leaving groups may be present in said position. Examples of such equivalent leaving groups include groups such as alkoxide groups such as —OCH$_3$, alkylthio groups such as —SCH$_3$ and phosphate groups such as

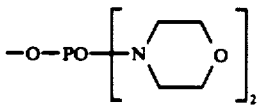

Reactions to provide alkoxide and alkylthio groups are well known; see, for example, G. A. Archer and L. H. Sternbach, Journal of Organic Chemistry, 29, 231 (1964) and U.S. Pat. No. 3,681,341.

A compound of formula VIII is then condensed with a nitroalkane of the general formula

IX wherein R$^{b'}$ represents hydrogen or lower alkyl to give a compound of the general formula

X

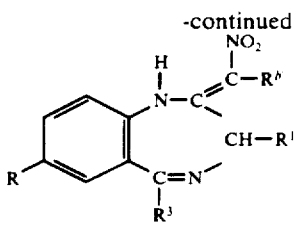

wherein R, R$^1$, R$^3$ and R$^{b'}$ have the significance given earlier.

The reaction of a compound of formula VIII with a nitroalkane of formula IX (e.g., nitromethane, nitroethane, etc.) is carried out in the presence of a base which is sufficiently strong to generate the nitroalkane anion. Suitable bases include alkali metal and alkaline earth metal alkoxides (e.g., potassium tert. butoxide), amides (e.g., lithium amide) and hydrides (e.g., sodium hydride). The reaction is preferably carried out in an inert solvent such as dimethylformamide, dimethylsulfoxide or an ether (e.g., tetrahydrofuran) at a temperature below or above room temperature (e.g., in the range of -50° C. to 150° C.), preferably at about room temperature.

A compound of formula X is then reduced by catalytic hydrogenation (e.g., using hydrogen in the presence of Raney nickel) or by means of a reducing agent such as lithium aluminum hydride to give a compound of the general formula

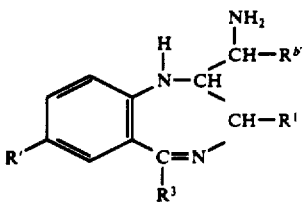
XI wherein R$^1$, R$^3$ and R$^{b'}$ have the significance given earlier and R' represents a halogen atom or an amino or trifluoromethyl group.

The above definition of R' in formula XI results from the conversion of a nitro group into an amino group under the conditions used in the reduction of a compound of formula X.

Solvents suitable for the hydrogenation in the presence of Raney nickel include alkanols (e.g., ethanol), ethers (e.g., tetrahydrofuran, diethyl ether, etc.), hydrocarbons (e.g., toluene) and dimethylformamide. The temperature at which this catalytic hydrogenation is carried out may be above or below room temperature (e.g., −50° C. to 150° C.). This catalytic hydrogenation may be carried out with or without pressure (e.g., a pressure of one atmosphere or above).

Solvents suitable for the reduction using a reducing agent such as lithium aluminum hydride include ethers such as tetrahydrofuran, dioxane and diethyl ether and mixtures of ethers and hydrocarbons such as tetrahydrofuran and benzene. This reduction may be carried out at a temperature of from below room temperature to the reflux temperature of the mixture, preferably at a temperature in the range of −50° C. to 60° C.

A compound of formula XI is then acylated with an acylating agent yielding the moiety R$^a$CO—, in which R$^a$ represents hydrogen or lower alkyl, such as an acid halide or acid anhydride (e.g., acetic anhydride and acetyl chloride) to give a compound of the general formula

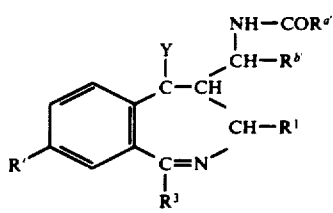

XII wherein $R^1$, $R^3$, $R^{a'}$ and $R^{b'}$ have the significance given earlier, $R'$ has the same significance as in formula XI and Y represents a hydrogen atom or the moiety $R^{a'}$CO—.

The acylation of a compound of formula XI may yield a mixture consisting of the predominant monoacylated product (i.e., in which the amino group is converted into a —NH—COR$^{a'}$ group) and the diacylated product in which both the amino group and nitrogen atom in the 1-position are acylated. The yield of diacylated product may be increased by subjecting a compound of formula XI to more rigorous conditions (i.e., the use of excess acylating agent and increased acylation time).

The acylation is preferably carried out in the presence of an aqueous or non-aqueous solvent (e.g., water, methylene chloride, benzene, chloroform, etc.) and preferably in the presence of an acid acceptor such as an organic base (e.g., an alkali metal carbonate) or an inorganic base (e.g., triethylamine or pyridine).

A compound of formula XII is subsequently cyclized to yield a compound of the general formula

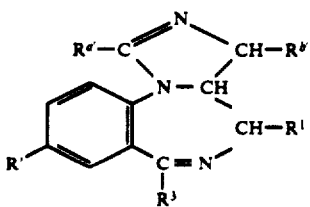

XIII wherein $R^1$, $R^3$, $R^{a'}$ and $R^{b'}$ have the significance given earlier and $R'$ has the significance given in formula XI.

The cyclization of a compound of formula XIII is carried out using a dehydrating agent such as phosphorus pentoxide, polyphosphoric acid or other suitable acid catalysts (e.g., an organic or inorganic acid such as concentrated sulfuric acid). A solvent is not required, but a solvent such as an aromatic hydrocarbon (e.g., toluene or xylene) may be used. The cyclization is carried out at a temperature of from about 100° C. to 200° C.

A compound of formula XI can also be reacted with an acylating agent such as an orthoester (e.g., triethylorthoacetate), an orthoamide (e.g., the N,N-dimethylformamide dimethyl acetal) or tris(dimethylamino)methane, if desired in the presence of an acid catalyst such as an organic acid (e.g., paratoluenesulfonic acid) or an inorganic acid (e.g., phosphoric acid) and at room temperature or a temperature above room temperature (e.g., 25° C. to 150° C.), in which instance the cyclization to a compound of formula XIII occurs spontaneously. Other useful acylating agents include esters (e.g., methyl acetate), amides (e.g., acetamide), nitriles (e.g., acetonitrile) and ester imidates.

A compound of formula XIII is then dehydrogenated to yield an imidazobenzodiazepine of the general formula

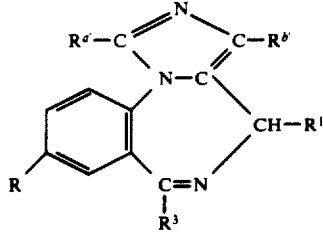

XIV wherein $R^1$, $R^3$, $R^{a'}$ have the significance given earlier and $R'$ has the significance given in formula XI.

The dehydrogenation of a compound of formula XIII is preferably carried out using manganese dioxide or palladium-on-carbon, although potassium permanganate may also be used. Solvents which may be used include chlorinated hydrocarbons, aromatic hydrocarbons, dimethylformamide, etc. The dehydrogenation is carried out at room temperature or at a temperature above room temperature (e.g., in the range of from about 25° C. to 200° C.).

The foregoing procedure may be carried out from compounds of formulae X or XI without isolation of any further intermediate compounds.

Compounds corresponding to formula XIV but wherein $R^{b'}$ represents a hydroxymethyl group can be prepared as follows:

A compound of formula VIII or a corresponding phosphate is reacted with dimethylmalonate, under the conditions described earlier for the reaction of these compounds with a nitroalkane of formula IX, to give a compound of the general formula

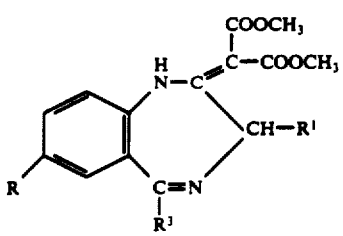

XV wherein R, $R^1$ and $R^3$ have the significance given earlier which is then converted into a compound of the general formula

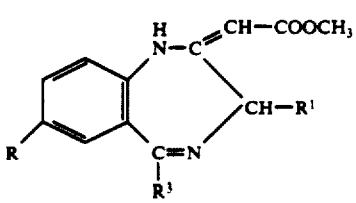

XVI wherein R, $R^1$ and $R^3$ have the significance given earlier by refluxing with methanolic potassium hydroxide. Upon treatment with nitrous acid (e.g., by adding sodium nitrite to a solution of a compound of formula XVI in glacial acetic acid) there is formed a compound of the general formula

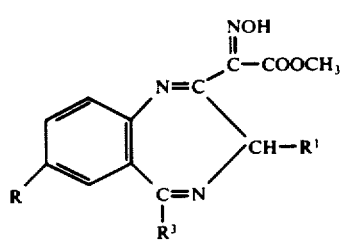

XVII wherein R, R¹ and R³ have the significance given earlier which is then catalytically hydrogenated (e.g., in the presence of Raney nickel) to a compound of the general formula

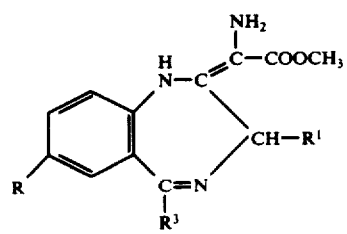

XVIII wherein R, R¹ and R³ have the significance given earlier which is then treated with an orthoester of the general formula

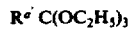

XIX wherein $R^a$ has the significance given earlier to yield a compound of the general formula

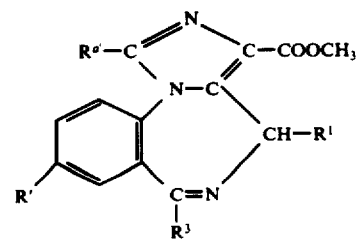

XX wherein R', R¹, R³ and $R^a$ have the significance given earlier. The carbomethoxy group in the 3-position of the compound of formula XX can be converted into the hydroxymethyl group by means of lithium aluminum hydride.

1-Hydroxymethyl-4H-imidazo[1,5-a][1,4]benzodiazepines can be prepared starting from corresponding 1-methyl compounds. By treatment with an N-oxide providing agent such as m-chloroperbenzoic acid, there can be obtained three different N-oxides, viz. the 5-oxide, the 2-oxide and the 2,5-dioxide, which can be separated by chromatography. The 2-oxide function can be selectively rearranged with acetic anhydride to give a 1-acetoxymethyl-2-desoxy compound and it is thus not necessary to separate the 2-oxide and the 2,5-dioxide for the preparation of the aforementioned 1-acetoxymethyl-2-desoxy compound since the 5-oxide function of a product obtained by subjecting a 2,5-dioxide to the said selective rearrangement can be reduced by phosphorous trichloride. The acetoxymethyl group in the 1-position of the compounds thus obtained can be easily converted into the hydroxymethyl group, e.g., by means of sodium methoxide in methanol.

It will be appreciated that when a compound of formula XI or XVIII in which R' represents an amino group is acylated, then such amino group may be acylated to an acylamino group. An acylamino group can be converted back into an amino group by mild hydrolysis. It will also be appreciated that compounds in which R' represents an amino group can be converted into corresponding nitro compounds by the well known Sandmeyer reaction; see, for example, E. R. Ward, C. D. Johnson and J. G. Hawkins, J. Chem. Soc., 894 (1960).

The starting materials of formula III hereinbefore can be prepared in the same manner as described hereinbefore for the manufacture of the corresponding compounds of formula I, but using appropriate compounds in which R represents a hydrogen atom.

The compounds of formula I hereinbefore form acid addition salts with inorganic acids (e.g., hydrohalic acids such as hydrochloric acid and hydrobromic acid, sulfuric acid, phosphoric acid and nitric acid) and with organic acids (e.g., acetic acid, succinic acid, glycolic acid, lactic acid, gluconic acid, tartaric acid, citric acid, maleic acid, malic acid, fumaric acid, methanesulfonic acid, paratoluenesulfonic acid, oxalic acid, ascorbic acid, benzoic acid, hydroxyethane sulfonic acid, 1,2-diethane sulfonic acid, etc.). The pharmaceutically acceptable acid addition salts are preferred. The acid addition salts can be prepared according to well known methods; for example, by treating a base with an appropriate acid. An acid addition salt may also be converted into a different acid addition salt by means of a suitable anion exchange resin (e.g., Amberlite IRA-401 in the chloride form).

The compounds of formula I hereinbefore and their acid addition salts possess sedative, muscle relaxant and anticonvulsant activity. Of particular interest are those pharmaceutically acceptable acid addition salts which are water soluble since they can be readily administered by injection; for example, in dentistry for the induction of anaesthesia and in the management of acute convulsive disorders and status epilepticus.

The anticonvulsant activity of the substituted phenyl ketones of the present invention is demonstrated by administering them to mice and then subjecting the thus-treated mice to the well known pentatetramethylenetetrazole test. In this test, L-phenylalanyl-N-(2-benzoyl-4-chlorophenyl)-N-methylglycinamide hydrobromide, which has an $LD_{50}$ of 70 mg/kg i.v. in mice, has an $ED_{50}$ of 2.0 mg/kg i.v. in mice. Also in this test, 5-chloro-2'-fluoro-2-[5-(L-leucylaminomethyl)-2-methyl-1-imidazolyl]benzophenone, which has an $LD_{50}$ of 119 mg/kg i.v. in mice, has an $ED_{50}$ of 2.0 mg/kg i.v. in mice. The muscle relaxant activity can be demonstrated in the well known rotating rod test. In this test, L-phenylalanyl-N-(2-benzoyl-4-chlorophenyl)-N-methylglycinamide hydrobromide has an $ED_{50}$ of 4.2 mg/kg i.v. in mice. Also in this test, 5-chloro-2'-fluoro-2-[5-(L-leucylaminomethyl)-2-methyl-1-imidazolyl]benzophenone has an $ED_{50}$ of 20 mg/kg i.v. in mice.

The compounds of formula I and their pharmaceutically acceptable acid addition salts may be used as medicaments; for example, in the form of pharmaceutical preparations which contain them in association with a compatible pharmaceutical carrier material. This carrier material can be an organic or inorganic carrier material suitable for enteral or parenteral administration (e.g., water, lactose, gelatin, starches, magnesium stearate, talc, vegetable oils, gums, polyalkyleneglycols, petroleum jelly, etc.). The pharmaceutical preparations can be made up in a solid form (e.g., as tablets, dragees, capsules, etc.) or in a liquid form (e.g., solutions suspensions or emulsions). Pharmaceutical preparations in a form adapted for injection purposes are preferred. The pharmaceutical preparations may be subjected to conventional pharmaceutical operations such as sterilization and/or may contain conventional pharmaceutical adjuvants such as preservatives, stabilizers, wetting agents, emulsifiers, buffers, etc.

The dosages in which the compounds of formula I and their pharmaceutically acceptable acid addition salts may be administered can vary depending on the requirements of the patient and the directions of the attending physician. A dosage of from 0.01 mg/kg/day to 1 mg/kg/day is, however, preferred.

The following examples illustrate the process provide by the present invention. The structure of all products obtained was confirmed by standard procedures including infrared and nuclear magnetic resonance spectroscopy.

EXAMPLE 1

A. The Preparation of the Starting Material i. 100 g. of 7-bromo-1,3-dihydro-5-(2-pyridyl)-2H-1,4-benzodiazepin-2-one were dissolved in 750 ml. of 2-N hydrochloric acid and left at room temperature overnight. The solution was evaporated to an oil which was dissolved in water and re-evaporated. The final traces of water were removed by shaking the oil with 50% methanol/toluene followed by evaporation. This treatment was repeated three times with 50% methanol/toluene and twice with toluene. There was obtained a pale-yellow to orange solid which was dried at 50° C. under a vacuum. The product was characterised by its spectral data and was shown by titration to contain 2.5 moles of hydrogen chloride to one mole of 2-amino-N--(4-bromo-2-picolinoylphenyl)acetamide (133.5 g; 99%). After prolonged drying over sodium hydroxide, there was obtained an analytical sample which was stoichiometric.

Analysis for $C_{14}H_{14}BrCl_2N_3O_2$ (407.11): Calculated: C: 41.31, H: 3.47; N: 10.32; Br: 19.63; Cl: 17.42 Found: C: 41.02; H: 3.61; N: 10.11; Br: 20.08; Cl: 17.82.

ii. 7.24 g. of N-benzyloxycarbonyl-L-phenylalanine N-hydroxysuccinimide ester were dissolved in 80 ml. of dimethylformamde, the solution was cooled to −20° C. and 8.48 g. of the dihydrochloride, prepared as described in paragraph (i), were added. 6.16 ml. of N-ethylmorpholine were then added over a period of 0.5 hour to the vigorously stirred suspension. The resulting mixture was subsequently stirred for 1 hour at −20° C. and overnight at room temperature. The solvent was removed in vacuo and the residue dissolved in a mixture of chloroform and water. The layers were separated and the aqueous layer extracted with a further portion of chloroform. The combined organic phases were washed five times with water, dried over magnesium sulphate and evaporated to an oil. Crystallisation from hot ethanol yielded 10.0 g. (64%) of (N-benzyloxycarbonyl-L-phenylalanyl)-N-(4-bromo-2-picolinoylphenyl)glycinamide of melting point 157°-183° C. (slow decomposition).

Analysis for $C_{31}H_{27}BrN_4O_5$ (615.50): Calculated: C: 60.49; H: 4.42; N: 9.10; Found: C: 60.44; H: 4.41; N: 8.90.

B. The Process 4.0 g. of (N-benzyloxycarbonyl-L-phenylalanyl)-N-(4-bromo-2-picolinoylphenyl)gylcinamide were stirred for 1 hour in a solution of 35% hydrogen bromide in glacial acetic acid. Dry diethyl ether was then added and the separated solid was filtered off, washed with diethyl ether and dried in vacuo. The crude product was dissolved in a minimum amount of dry methanol and treated with ethyl acetate, whereby the product separated. There were obtained 3.8 g. (91%) of L-phenylalanyl-N-(4-bromo-2-picolinoylphenyl)glycinamide dihydrobromide of melting point 182° C. (decomposition); $[\alpha]^{20}D = +28.4°$ ($c = 1$ in water).

Analysis for $C_{23}H_{23}Br_3N_4O_3$ (643.20): Calculated: C: 42.95; H: 3.60; N: 8.71; Br: 37.27. Found: C: 42.53; H: 3.68; N: 8.35; Br: 37.04.

2.0 g. of the foregoing dihydrobromide were dissolved in 10 ml. of water and dilute ammonium hydroxide solution was added slowly with stirring until the solution was basic. The yellow oil which separated crystallised on standing. The product was filtered off, washed with water, dried in vacuo and recrystallised from ethanol/water. There were obtained 1.18 g. (79%) of the free base, L-phenylalanyl-N-(4-bromo-2-picolinoylphenyl)glycinamide, of melting point 60° C. (decompositon) and $[\alpha]_D^{20} = +26.7°$ ($c = 1$ in 1-N hydrochloric acid).

Analysis for $C_{23}H_{21}BrN_4O_3$ (481.36): Calculated: C: 57.39; H: 4.40; N: 11.64; Br: 16.60. Found: C: 56.96; H: 4.42; N: 11.48; Br: 16.42.

EXAMPLE 2

In a manner analogous to that described in Example 1, there was obtained glycyl-N-(4-bromo-2-picolinoylphenyl)-glycinamide of melting point 97°-100° C.

Analysis for $C_{16}H_{15}BrN_4O_3$ (391.23): Calculated: C: 49.11; H: 3.87; N: 14.32; Br: 20.42. Found: C: 48.95; H: 3.92; N: 14.15; Br: 20.55.

EXAMPLE 3

In a manner analogous to that described in Example 1, there was obtained L-lysyl-N-(4-bromo-2-picolinoylphenyl)-glycinamide trihydrobromide of melting point 220° C. (decomposition); $[\alpha]_D^{20} = +16.8°$ (c = 1 in water).

Analysis for $C_{20}H_{27}Br_4N_5O_3$ (705.11): Calculated: C: 34.07; H: 3.86; N: 9.93; Br: 45.34; Br ion: 34.00 Found: C: 34.29; H: 4.25; N: 9.73; Br: 44.60; Br ion: 33.32; $H_2O$: 0.96.

Water-free: C: 34.62; H: 4.18; N: 9.82; Br: 45.03; Br ion: 33.64.

EXAMPLE 4

A. The preparation of the starting material 3.18 g. of N-benzyloxycarbonyl-L-isoleucine were dissolved in 25 ml. of dry tetrahydrofuran and cooled to −10° C. 1.57 ml. of isobutylchloroformate and 1.52 ml. of N-ethylmorpholine were added and the resulting solution was stirred at −10° C. for 20 minutes. 4.24 g. of 2-amino-N-(4-bromo-2-picolinoylphenyl)-acetamide dihydrochloride, prepared as described in part A)i) of Example 1, were added an the resulting suspension was cooled to −20° C. 3.13. ml. of N-ethylmorpholine in 25 ml. of dimethylformamide were added to the vigorously stirred suspension over a period of 0.5 hour. The resulting mixture was stirred at −20° C. for a further 40 minutes and left at room temperature overnight. The product was worked up in a manner analogous to that described in part A)ii) of Example 1. Recrystallisation from ethanol yielded 4.2 g (60%) of (N-benzyloxycarbonyl-L-isoleucyl)-N-(4-bromo-2-picolinoylphenyl)-glycinamide of melting point 714°-176° C.

Analysis for $C_{28}H_{29}BrN_4O_5$ (581.48): Calculated: C: 57.84; H: 5.03; N: 9.64; Br: 13.74. Found: C: 57.84; H: 5.02; N: 9.39; Br: 13.67.

B. The process 2.0 g. of (N-benzyloxycarbonyl-L-isoleucyl)-N-(4-bromo-2-picolinoylphenyl)glycinamide were stirred for 1 hour in a solution of 35% hydrogen bromide in glacial acetic acid. Dry diethyl ether was then added and the solid which separated was filtered off, washed with diethyl ether and dried in vacuo. Two precipitations from methano/ethyl acetate yielded 1.9 g. (91%) of L-isoleucyl-N-(4-bromo-2-picolinoylphenyl)glycinamide dihydrobromide of melting point 174° C. (decomposition).

1.0 g. of the foregoing dihydrobromide was dissolved in 10 ml. of water and dilute ammonium hydroxide solution was added with stirring until the solution was basic. The resulting oil crystallised on standing, the crystals were filtered off, washed with water and dried in vacuo to give 0.65 g. (89%) of the free base, L-isoleucyl-N-(4-bromo-2-picolinoylphenyl)glycinamide, of melting point from 54° C. (slow decomposition); $[\alpha]_D^{20} = -29.6°$ (c = 1 in 1-N hydrochloric acid).

Analysis for $C_{20}H_{23}BrN_4O_3$ (447.34): Calculated: C: 53.70; H: 5.18; N: 12.52; Br: 17.87. Found: C: 52.97; H: 5.23; N: 12.26; Br: 17.85; $H_2O$: 1.75.

Water-free: C: 53.37; H: 5.18; N: 12.35; Br: 17.98.

EXAMPLE 5

In a manner analogous to that described in Example 4, but using $N^\alpha$-benzyloxycarbonyl-L-arginine monohydrobromide, there was obtained L-arginyl-N-(4-bromo-2-picolinoylphenyl)-glycinamide trihydrobromide hydrate as a lyophilised solid $[\alpha]_D^{20} = +10.9°$ (c = 1 in water).

Analysis for $C_{20}H_{29}Br_4N_7O_4$ (751.14): Calculated: C: 32.00; H: 3.89; N: 13.05; Br ion 31.92. Found: C: 31.85; H: 3.88; N: 13.00; Br ion 32.20.

EXAMPLE 6

In a manner analogous to that described in Example 4, but using N-benzyloxycarbonyl-L-glutamic acid γ-tert-butyl ester, there was obtained α-glutamyl-N-(4-bromo-2-picolinoylphenyl)glycinamide hydrobromide (1:1.85) of melting point 153°-170° C (slow decomposition); $[\alpha]_D^{20} = +20.0°$ (c = 1 in water).

Analysis for $C_{19}H_{19}BrN_4O_5 \cdot 1.85$ HBr (612.98): Calculated: C: 37.23; H: 3.43; N: 9.14; Br: 37.15. Found: C: 36.68; H: 3.69; N: 8.64; Br: 36.55; $H_2O$: 1.28.

Water-free: C: 37.16; H: 3.59; N: 8.75; Br: 37.02.

EXAMPLE 7

A. The preparation of the starting material

In a manner analogous to that described in Example 4A there was obtained ($N^\alpha,N^\epsilon$-ditertbutoxycarbonyl-L-lysyl)-N-(4-bromo-2-picolinoylphenyl)glycinamide of melting point 135°-137° C.

Analysis for $C_{30}H_{40}BrN_5O_7$ (662.59): Calculated: C: 54.38; H: 6.09; N: 10.57; Br: 12.06. Found: C: 54.33; H: 5.87; N: 10.34; Br: 12.24.

B. The process 1.0 g of ($N^\alpha,N^\epsilon$-ditertbutoxycarbonyl-L-lysyl)-N-(4-bromo-2-picolinoylphenyl)glycinamide was stirred for 1 hour in a solution of hydrogen chloride in dioxan (4-M). Diethyl ether was added and the solid which separated was filtered off, washed with diethyl ether and dried. The solid was dissolved in methanol and precipitated with ethyl acetate. The precipitate was dissolved in 20 ml of water and, after extraction with chloroform, the aqueous solution was lyophilised to yield 0.7 g (88%) of L-lysyl-N-(4-bromo-2-picolinoylphenyl)glycinamide trihydrochloride 1.5 $H_2O$; $[\alpha]_D^{20} = +20.1°$ (c = 1 in water).

Analysis for $C_{20}H_{27}BrCl_3N_5O_3 \cdot 1.5$ $H_2O$ (598.76): Calculated: C: 40.12; H: 5.05; N: 11.70; Cl: 17.76. Found: C: 40.27; H: 4.92; N: 11.57; Cl: 17.62.

EXAMPLE 8

In a manner analogous to that described in Example 4, there was obtained L-γ-glutamyl-N-(4-bromo-2-picolinoylphenyl)-glycinamide of melting point 158°-161° C. (decomposition); $[\alpha]_D^{20} + 121.1°$ (c = 1 in 1-N-hydrochloric acid).

Analysis for $C_{19}H_{19}BrN_4O_5$ (463.30): Calculated: C: 49.26; H: 4.13; N: 12.09; Br: 17.25; Found: C: 48.26; H: 4.40; N: 11.94; Br: 17.35; $H_2O$: 1.24.

Water-free: C: 48.87; H: 4.31; N: 12.09; Br: 17.57.

EXAMPLE 9

In a manner analogous to that described in Example 1, there was obtained L-alanyl-N-(4-bromo-2-picolinoylphenyl)-glycinamide pf melting point 76°-78° C; $[\alpha]_D^{20} = +17.4°$ (c = 1.0225 in methanol).

Analysis for $C_{17}H_{17}BrN_4O_3$ (405.26): Calculated: C: 50.38; H: 4.23; N: 13.82; Br: 19.71. Found: C: 50.43; H: 4.21; N: 13.56; Br: 19.74.

EXAMPLE 10

A. The preparation of the starting material 6.56 g. of tertbutoxycarbonyl-L-leucyl N-hydroxysuccinimide ester were dissolved in 80 ml. of dimethylformamide, the solution was cooled to −20° C. and 8.48 g. of 2-amino-N-(4-bromo-2-picolinoylphenyl)acetamide dihydrochloride were added. 6.16 ml. of N-ethylmorpholine were then added over a period of 30 minutes to the vigorously stirred suspension. The mixture was then stirred for one hour at −20° C. and overnight at room temperature.

The working-up was carried out in the same manner as described in Example 1A)ii). The resulting oil was crystallised from a mixture of ethanol and water and recrystallised from the same solvent mixture to yield 5.1 g. (47%) of pure (N-tertbutoxycarbonyl-L-leucyl)-N-(4-bromo-2-picolinoylphenyl) glycinamide of melting point 129°-132° C.

Analysis for $C_{25}H_{31}BrN_4O_5$ (547.46): Calculated: C: 54.85; H: 5.71; N: 10.23; Br: 14.60. Found: C: 54.73; H: 5.83; N: 10.02; Br: 14.95.

B. The process 2.0 g. of (N-tertbutoxycarbonyl-L-leucyl)-N-(4-bromo-2-picolinoylphenyl)glycinamide were stirred for one hour in a solution of hydrogen chloride in dioxan (4-M). Ethyl acetate was added and the solid which separated was filtered off, washed with ethyl acetate and dried in vacuo. The solid was dissolved in a minimum amount of methanol and the product, L-leucyl-N-(4-bromo-2-picolinoylphenyl)glycinamide hydrochloride, separated on the addition of ethyl acetate.

The hydrochloride was dissolved in 50 ml. of water and dilute ammonium hydroxide solution was added slowly with stirring until the solution was basic. The yellow oil which separated crystallised on standing.

The product was filtered off, washed with water and dried in vacuo. There was obtained 0.85 g. (53%) of L-leucyl-N-(4-bromo-2-picolinoylphenyl)-glycinamide of melting point 53° C. (decomposition); $[\alpha]_D^{20} = +26.0°$ (c = 1 in 1-N hydrochloric acid).

Analysis for $C_{20}H_{23}BrN_4O_3$ (447.34): Calculated: C: 53.70; H: 5.18; N: 12.52. Found: C: 53.35; H: 5.14; N: 12.21; $H_2O$: 1.32.

Water-free: C: 54.06; H: 5.06; N: 12.37.

EXAMPLE 11

A. The preparation of the starting material 15.9 g. of N-benzyloxycarbonylglycylglycine were suspended in 600 ml. of dry 1,2-dimethoxyethane and the suspension was cooled to −5° C. 6.06 g. of N-methylmorpholine and 8.22 g. of isobutylchloroformate were added and the resulting mixture was stirred at −5° C. to −10° C. for 2 hours. Unreacted starting material and N-methylmorpholine hydrochloride were separated by filtration and the filtrate (stored at −5° C. to 0° C) was added portionwise over a period of several hours to a refluxing solution of 14.7 g. of 5-chloro-2-methylaminobenzophenone in 200 ml. of dry 1,2-dimethoxyethane. The resulting solution was then stirred under reflux overnight.

The mixture was evaporated in vacuo and the residue taken up in 600 ml. of ethyl acetate, washed three times with 150 ml. of water each time and with 150 ml. of saturated sodium chloride solution, dried over ahydrous magnesium sulphate and then evaporated to give 30 g. of a yellow gum. Column chromatography of this gum on Florisil using mixtures of benzene and methanol yielded 12 g. (40%) of pure (N-benzyloxy-carbonyl-glycyl)-N-(2-benzoyl-4-chlorophenyl)-N-methyl-glycinamide as an almost colorless light-sensitive gum which was characterised by its spectroscopic properties and elemental analysis.

Analysis for $C_{26}H_{24}ClN_3O_5$ (493.95): Calculated: C: 63.23; H: 4.90; N: 8.51; Cl: 7.18. Found: C: 63.61; H: 4.87; N: 8.37; Cl: 7.02.

The process 9.87 g. of (N-benzyloxycarbonylglycyl)-N-(2-benzoyl-4-chlorophenyl)-N-methylglycinamide were dissolved in 50 ml. of glacial acetic acid and treated with 50 ml. of a 30% solution of hydrogen bromide in glacial acetic acid. The resulting solution was stirred at room temperature for 1 hour, treated with excess dry diethyl ether and the separated solid washed with serveral additional portions of dry diethyl and then dried in vacuo. The thus-obtained hygroscopic solid (7.5 g.) was mainly glycyl-N-(2-benzoyl-4-chlorophenyl)-N-methyl-glycinamide hydrobromide of melting point 140°-150° C. (decomposition).

Analysis for $C_{18}H_{18}ClN_3O_3$. 1.2 HBr (456.9): Calculated: C: 47.32; H: 4.24; N: 9.20; Br ion: 20.99. Found: C: 46.86; H: 4.59; N: 9.11; Br ion: 20.70.

4.6 g. of the foregoing crude hydrobromide were purified by solution in 100 ml. of 0.2-N sodium acetate and extraction of the solution with ether in order to remove by-products. The aqueous solution was then basified with excess sodium carbonate and extracted with dichloromethane to yield, after evaporation and de-gassing in vacuo, glycyl-N-(2-benzoyl-4-chlorophenyl)-N-methylglycinamide as an almost colorless light-sensitive glassy foam which was characterised by its spectroscopic properties.

EXAMPLE 12

A. The preparation of the starting material

In a manner analogous to that described in Example 8A), there was obtained (N-benzyloxycarbonylglycyl)-N-(4-bromo-2-picolinoylphenyl) glycinamide of melting point 139°-141° C. (from ethanol).

B. The process

In a manner analogous to that described in Example 8B), (N-benzyloxycarbonylglycyl)-N-(4-bromo-2-picolinoylphenyl)-glycinamide was converted into glycyl-N-(4-bromo-2-picolinoylphenyl)glycinamide of melting point 97°-100° C.

EXAMPLE 13

A. The preparation of the starting material a. 20.9 g. of N-benzyloxycarbonylglycine were suspended in 1500 ml. of dry 1,2-dimethoxyethane and the suspension was cooled to −20° C. 10.1 g. of N-methylmorpholine and 13.7 g. of isobutylchloroformate were added, the resulting solution was stirred at −20° C. for 1 hour and then filtered. The filtrate (stored at −10° C. to 0° C) was added portionwise over a period of several hours to a refluxing solution of 24.55 g. of 5-chloro-2-methylaminobenzophenone in 200 ml. of 1,2-dimethoxyethane, the resulting mixture was boiled overnight and then evaporated to dryness in vacuo. The yellow residue was dissolved in ethyl acetate, washed with two portions of water and one portion of saturated sodium chloride solution, drived over anhydrous magnesium sulphate and then evaporated in vacuo. Column chromatography of the residue on Florisil using mixtures of benzene and chloroform yielded 35 g. (80%) of pure 2-(N-benzyloxycarbonylamino)-N-(2-benzoyl-4-chloro-phenyl)-N-methylacetamide as a pale yellow gum.

Analysis for $C_{24}H_{21}ClN_2O_4$ (436.9): Calculated: C: 65.98; H: 4.85; N: 6.41. Found: C: 65.91; H: 5.03; N: 6.51.

43.7 g. of 2-(N-benzyloxycarbonylamino)-N-(2-benzoyl-4-chlorophenyl)-N-methylacetamide were dissolved in 200 ml. of a 30% solution of hydrogen bromide in glacial acetic acid and the resulting solution was stirred overnight at room temperature. The mixture was added slowly to a large excess (2000 ml) of dry ether with vigorous stirring. The product which separated was allowed to settle and the supernatant liquors were decanted off. The residue was triturated with 150 ml. of acetone and the product filtered off, washed consecutively with the minimum amount of acetone and dry ether and dried in vacuo to give 29.5 g. (77%) of 2-amino-N-(2-benzoyl-4-chlorophenyl)-N-methylacetamide hydrobromide as a white hygroscopic powder of melting point 194°-195° C. (decomposition).

Analysis for $C_{16}H_{16}BrClN_2O_2$ (383.7): Calculated: C: 50.10; H: 4.21; N: 7.30; Br ion: 20.83. Found: C: 44.98; H: 3.83; N: 7.15; Br ion: 21.14.

b. 84 g. of N-benzyloxycarbonylglycine were suspended in 500 ml. of alcohol-free chloroform and the suspension was cooled to −20° C. The stirred suspension was treated portionwise over a period of 15 minutes with 90 g. of phosphorus pentachloride and the stirring was continued until a clear solution was obtained. At this point, the cold mixture was added dropwise over a period of 30 minutes to a cold (−5° C.) vigorously stirred emulsion consisting of 82 g. of 5-chloro-2-methyl-aminobenzophenone, 347 g. of potassium bicarbonate, 700 ml. of chloroform and 1400 ml. of water. The resulting mixture was stirred for a further 1 hour at −5° C. And then overnight at room temperature. The stirring was then discontinued and the liquid phases allowed to separate. The chloroform layer was washed three times with 500 ml. of water each time and evaporated in vacuo to give 150.7 g. of a viscous yellow gum which was shown by physical methods to be almost pure (above 95%) 2-(N-benzyloxycarbonylamino)-N-(2-benzoyl-4-chlorophenyl)-N-methylacetamide.

The product obtained according to the preceding paragraph was dissolved in 650 ml of a 30% solution of hydrogen bromide in glacial acetic acid and treated in an identical manner to that described in part (a) of this Example to give 2-amino-N-(2-benzoyl-4-chlorophenyl)-N-methylacetamide hydrobromide in a 77% overall yield from 5-chloro-2-methylaminobenzophenone.

c. 3.96 g of N-benzyloxycarbonyl-L-phenylalanine N-hydroxysuccinimide ester were dissolved in 50 ml of dry dimethylformamide. The resulting solution was cooled to −20° C and there were added 3.84 g of 2-amino-N-(2-benzoyl-4-chlorophenyl)-N-methylacetamide hydrobromide followed by the dropwise addition of 1.15 g of N-ethylmorpholine. The resulting mixture was vigorously stirred for 1 hour at −20° C and then overnight at room temperature. The solvent was evaporated in vacuo and the residue dissolved in a mixture of dichloromethane and water. The organic and aqueous layers were separated and the aqueous phase extracted with further portions of dichloromethane. The combined organic phases (250 ml) were washed three times with 50 ml of water each time, dried over anhydrous magnesium sulphate and evaporated in vacuo to give 5.8 g of a yellow oily residue which was shown by physical methods to consist of a mixture of 7-choloro-1,3-dihydro-1-methyl-5-phenyl-2H-1,4-benzodiazepin-2-one and (N-benzyloxycarbonyl-L-phenylalanyl)-N-(2-benzoyl-4-chlorophenyl)-N-methylglycinamide in the approximate proportions of 1:3.

The foregoing mixture can be purified by column chromatography on Florisil to give pure (N-benzyloxycarbonyl-L-phenylalanyl)-N-(2-benzoyl-4-chlorophenyl)-N-methylglycinamide as an almost colourless light-sensitive brittle foam; $[\alpha]_D^{20} = -13.6°$ (c = 1 in ethanol).

Analysis for $C_{33}H_{30}ClN_3O_5$ (584.1): Calculated: C: 67.86; H: 5.18; N: 7.19; Cl: 6.07. Found: C: 67.76; H: 5.08; N: 6.84; Cl: 6.16.

Alternatively, the foregoing mixture can be subjected directly to removal of the projecting group as follows:
B. The process
i. 5.8 g of the mixture aforesaid were dissolved in 20 ml of a 30% solution of hydrogen bromide in glacial acetic acid and the solution was stirred at room temperature for 3 hours. 200 ml of dry diethyl ether were then added. The solid which separated was collected and dissolved in 100 ml of water, treated with excess sodium carbonate and extracted with four 75 ml portions of diethyl ether. The combined ether extracts were then shaken with six 50 ml portions of 0.1-N acetic acid in order to separate the more strongly basic products from the more weakly basic byproduct (the benodiazepin-2-one). The combined aqueous acidic solution was washed with 100 ml of diethyl ether, made basic with excess sodium carbonate and extracted with four 75 ml portions of dichloromethane. The dichloromethane extracts were then combined, washed with saturated sodium chloride solution, dried over anhydrous magnesium sulphate and evaporated in vacuo. Thorough degassing in vacuo gave 3.1 g (68%) of pure L-phenylalanyl-N-(2-benzoyl-4-chlorophenyl)-N-methylglycinamide as an almost coulourless light-sensitive brittle foam; $[\alpha]_D^{20} = 11.6°$ (c = 1 in ethanol).

Analysis for $C_{25}H_{24}ClN_3O_3$ (449.9): Calculated: C: 66.74; H: 5.38; N: 9.34; Cl: 7.88. Found: C: 66.71; H: 5.47; N: 9.23; Cl: 8.14.

Treatment of the foregoing free base with an equimolar amount of anhydrous (+)-tartaric acid in warm isopropanol gave colourless crystals of the hydrogen (+)-tartrate of melting point 198°-200° C.

Analysis for $C_{29}H_{30}ClN_3O_9$ (600.00): Calculated: C: 58.05; H: 5.04; N: 7.00; Cl: 5.91. Found: C: 58.32; H: 4.98; N: 6.73; Cl: 5.90.

ii. 5.8 g of the mixture aforesaid were dissolved in 75 ml of dry nitromethane and a slow stream of hydrogen bromide was passed through the solution for 10–15 minutes. The solution was then stirred for a further 2 hours at room temperature and then treated with an excess of dry diethyl ether. The solid which separated was treated in an identical manner to that described in part (i) of this Example to give 2.4 g (53%) of L-phenylalanyl-N-(2-benzoyl-4-chlorophenyl)-N-methylglycinamide.

The foregoing free base was converted into the hydrochloride as follows:

4.5 g of L-phenylalanyl-N-(2-benzoyl-4-chlorophenyl)-N-methylglycinamide were dissolved in a minimum volume of methanol at room temperature and treated, by titration, with an exact equivalent of 1-N hydrochloric acid. The solvent was removed from the resultinhg solution by evaporation in vacuo at room temperature and finally by lyophilisation to give, in quantitative yield, L-phenylalanyl-N-(2-benzoyl-4-chlorophenyl)-N-methylglycinamide hydrochloride as a hydroscopic white light-sensitive amorphous powder of melting point 130°-150° C (slow decomposition): $[\alpha]_D^{20} = +41.7°$ (c = 1 in water).

Analysis for $C_{25}H_{25}Cl_2N_3O_2$ (486.4): Calculated: C: 61.74; H: 5.18; N: 8.64; Cl ion: 7.29. Found: C: 60.24; H: 5.22; N: 8.30; Cl ion: 7.31; $H_2O$: 2.17.

Water-free: C: 61.58; H: 5.08; N: 8.48; Cl ion: 7.47.

EXAMPLE 14

In a manner analogous to that described in Example 13, there was obtained glycyl-N-(2-benzoyl-4-chlorophenyl)-glycinamide of melting point 136°-138° C (from ethanol).

Analysis for $C_{17}H_{16}ClN_3O_3$ (345.79): Calculated: C: 59.05; H: 4.66; N: 12.15; Cl: 10.26. Found: C: 59.03; H: 4.63; N: 11.79; Cl: 10.26.

EXAMPLE 15

In a manner analogous to Example 13, there was obtained glycyl-N-(2-benzoyl-4-nitrophenyl)glycinamide of melting point 121°-123° C (from ethanol).

Analysis for $C_{17}H_{16}N_4O_5$ (356.34): Calculated: C: 57.31; H: 4.53; N: 15.72. Found: C: 57.54; H: 4.58; N: 15.73.

EXAMPLE 16

In a manner analogous to that described in Example 13, there was obtained L-prolyl-N-(2-benzoyl-4-nitrophenyl)glycinamide of melting point 165°-167° C.

EXAMPLE 17

In a manner analogous to that described in Example 13, there was obtained L-alanyl-N-(2-benzoyl-4-chlorophenyl)-N-methylglycinamide hydrochloride of melting point 115°-130° C (slow decomposition); $[\alpha]_D^{20} = +7.09°$ (c = 1 in water).

Analysis for $C_{19}H_{21}Cl_2N_3O_3$ (410.31): Calculated: C: 55.62; H: 5.16; N: 10.24; Cl ion: 8.64. Found: C: 55.86; H: 5.20; N: 9.95; Cl ion: 8.42.

EXAMPLE 18

A. The preparation of the starting material

In a manner analogous to that described in Example 13 A), there was obtained (N$^\alpha$,N$^\epsilon$-bisbenzyloxycarbonyl-L-lysyl)-N-(2-benzoyl-4-chlorophenyl)-N-methylglycinamide as an almost colourless light-sensitive gum; $[\alpha]_D^{20} = -9.3°$ (c = 1 in ethanol).

Analysis for $C_{38}H_{39}ClN_4O_7$ (699.2): Calculated: C: 65.28; N: 5.62; N: 8.02; Cl: 5.:7. Found: C: 64.90; H: 5.56; N: 7.84; Cl: 5.25.

B. The process i. (N$^\alpha$,N$^\epsilon$-Bisbenzyloxycarbonyl-L-lysyl)-N-(2-benzoyl-4-chlorophenyl)-N-methylglycinamide was converted using a 30% solution of hydrogen bromide in glacial acetic acid into L-lysyl-N-(2-benzoyl-4chlorophenyl)-N-metylglycinamide dihydrobromide which was obtained as a hygroscopic powder of melting point 145°-160° C (decomposition); $[\alpha]_D^{20} = +15.6°$ (c = 1 in water).

Analysis for $C_{22}H_{29}Br_2ClN_4O_3$ (592.8): Calculated: C: 44.58; H: 4.93; N: 9.45; Br ion: 26.96. Found: C: 43.58; H: 5.17; N: 9.21; Br ion: 27.43; $H_2O$: 0.99.

Water-free: C: 44.02; H: 5.11; N: 9.30; Br ion: 27.70.

Treatment of the foregoing dihydrobromide in aqueous solution by passage over an excess of an anion-exchange resin such as AMBERLITE IRA-401 in the chloride form followed by lyophilisation of the eluate gave, in quantitative yield, L-lysyl-N-(2-benzoyl-4-chlorophenyl)-N-methylglycinamide dihydrochloride as a hygroscopic white light-sensitive powder of melting point 125°-145° C (slow decomposition); $[\alpha]_D^{20} = +19.3°$ (c = 1 in water).

Analysis for $C_{22}H_{29}Cl_3N_4O_3$ (503.86): Calculated: C: 52.45; H: 5.80; N: 11.12; Cl: 21.12. Found: C: 51.58; H: 5.80; N: 11.18; Cl: 20.80; $H_2O$: 0.99.

Water-free: C: 52.10; H: 5.75; N: 11.29; Cl: 21.10.

ii. 1.4 g of (N$^\alpha$,N$^\epsilon$-bisbenzyloxycarbonyl-L-lysyl)-N-(2-benzoyl-4-chlorophenyl)-N-methylglycinamide were dissolved in 30 ml of dry dichloromethane, cooled to approximately −70° C and treated, while stirring, with 2 ml of pre-cooled boron trichloride. The mixture was stirred under anhydrous conditions at approximately −70° C for 30 minutes and then allowed to warm slowly to room temperature over a period of 2 hours. The mixture was evaporated to dryness in vacuo, the residue re-dissolved in 30 ml of fresh dry dichloromethane and the solution again evaporated to dryness in vacuo. This operation was repeated twice using dichloromethane and then four times using methanol in order to remove the residual boron compounds as volatile trimethyl borate. A concentrated methanolic solution of the residue was added slowly to 750 ml of anhydrous diethyl ether with vigorous stirring, the solid hygroscopic product collected by filtration and dried in vacuo. This product was dissolved in 30 ml of water, shaken with three 20 ml portions of ethyl acetate to remove traces of 5-chloro-2-methylaminobenzophenone and the aqueous solution lyophilised to give 0.7 g of L-lysyl-N-(2-benzoyl-4-chlorophenyl)-N-methylglycinamide dihydrochloride which was identical to that described in part (i) of this Example.

EXAMPLE 19

In a manner analogous to that described in Example 13 there was obtained L-leucyl-N-(2-benzoyl-4-chlorophenyl)-N-methylglycinamide in the form of a pale yellow gum; $[\alpha]_D^{20} = -2.2°$ (c = 1 in ethanol).

Analysis for $C_{22}H_{26}ClN_3O_3$ (415.9): Calculated: C: 63.54; H: 6.30; N: 10.10; Cl: 8.52. Found: C: 63.25; H: 6.69; N: 9.75; Cl: 8.33.

EXAMPLE 20

In a manner analogous to that described in Example 13, there was obtained L-phenylalanyl-N-(2-benzoyl-4-nitrophenyl)-glycinamide of melting point 144° - 146° C (from methanol); $[\alpha]_D^{20} = -29.4°$ (c = 1 in dioxan).

Analysis for $C_{24}H_{22}N_4O_5$ (446.47): Calculated: C: 64.56; H: 4.97; N: 12.55. Found: C: 64.39; H: 4.95; N: 12.74.

EXAMPLE 21

A. The preparation of the starting material

In a manner analagous to that described in Example 13A) there was obtained (N$^\alpha$,N$^\epsilon$,N$^\omega$-trisbenzyloxycarbonyl-L-arginyl)-N-(2-benzoyl-4-chlorophenyl)-N-methylglycinamide as an almost colourless light-sensitive brittle foam; $[\alpha]_d^{20} = -2.4°$ (c = 1 in ethanol).

Analysis for $C_{46}H_{45}ClN_6O_9$ (861.35): Calculated: C: 64.14; H: 5.27; N: 9.76; Cl: 4.12. Found: C: 63.44; H: 5.17; N: 9.59; Cl: 4.65.

Solvent-free*: C: 63.90; H: 5.20; N: 9.68; Cl: 3.91.

*The dichloromethane content was estimated by nuclear magnetic resonance spectroscopy to be 0.10 ± 0.02 moles.

Calculated for $C_{46}H_{45}ClN_6O_9$, 0.1 $CH_2Cl_2$ (869.84): C: 63.66; H: 5.24; N: 9.66; Cl: 4.80.

B. The process i. 5.0 g of (N$^\alpha$,N$^\epsilon$, N$^\omega$-trisbenzyloxycarbonyl-L-arginyl)-N-(2-benzoyl-4-chlorophenyl)-N-methylglycinamide were dissolved in 60 ml of dry dichloromethane, cooled to 0° C and treated, while stirring, with 4 ml of boron tribromide. The mixture was stirred under anhydrous conditions at 0° C for 2 hours and then allowed to warm to room temperature overnight. Excess boron tribromide was neutralised by the dropwise addition of a solution of anhydrous methanol in dry dichloromethane until no further reaction was observed. The mixture was evaporated to dryness in vacuo, the residue re-dissolved in 30 ml of anhydrous methanol and the solution again evaporated to dryness. This operation was repeated a further twice using methanol in order to remove the residual boron compounds as volatile trimethyl borate. A concentrated solution of the residue in methanol was added slowly to 1 liter of anhydrous diethyl ether with vigorous stirring. The solid hygroscopic product was collected by filtration and dried in vacuo. This produce was dissolved in 100 ml of water, shaken with three 50 ml portions of ethyl acetate to remove traces of 5-chloro-2-methylaminobenzophenone and the aqueous solution lyophilised to give 3.2 g of L-arginyl-N-(2-benzoyl-4-chlorophenyl)-N-methylglycinamide dihydrobromide as an almost colourless light-sensitive amorphous powder; $[\alpha]_D^{20} = +12.8°$ (c = 1 in water).

Analysis for $C_{22}H_{27}Br_2ClN_6O_3$ (620.77): Calculated: C: 42.56; H: 4.71; N: 13.53; Br ion: 25.74. Found: C: 40.74; H: 4.91; N: 13.29; Br ion: 26.08; $H_2O$: 1.89.

Water-free: C: 41.52; H: 4.79; N: 13.55; Br ion: 26.58.

Calculated for $C_{22}H_{25}ClN_6O_3$.2.1 HBr (631.29): C: 41.86; H: 4.65; N: 13.31; Br ion: 26.96.

The foregoing dihydrobromide was treated in a manner analogous to that described in part B) (i) of Example 18 to give, in quantitative yield, L-arginyl-N-(2-benzoyl-4-chlorophenyl)-N-methylglycinamide dihydrochloride as a white lightsensitive amorphous powder of melting point 155°–160° C (slow decomposition); $[\alpha]_D^{20} = +14.9°$ (c = 1 in water).

Analysis for $C_{22}H_{27}Cl_3N_6O_3$ (531.87): Calculated: C: 49.68; H: 5.49; N: 15.80; Cl: 19.99. Found: C: 48.47; H: 5.75; N: 15.84; Cl: 20.16; H$_2$O: 1.17.

Water-free: C: 49.04; H: 5.69; N: 16.03; Cl: 20.40.

Calculated for $C_{22}H_{25}ClN_6O_3$. 2.1 HCl (535.52): C: 49.34; H: 5.48; N: 15.69; Cl: 20.52.

EXAMPLE 22

A. The preparation of the starting material a. In a manner analogous to that described in Example 13A) (b) there was obtained 2-(N-benzyloxycarbonylamino)-N-(2-benzoyl-4-chlorophenyl)-N-methylpropionamide as a pale yellow gum; $[\alpha]_D^{20} = -3.75°$ (c = 1 in ethanol).

Analysis for $C_{25}H_{23}ClN_2O_4$ (450.92): Calculated: C: 66.60; H: 5.14; N: 6.21; Cl: 7.86. Found: C: 66.27; H: 5.18; N: 5.88.

The product obtained according to the preceding paragraph was dissolved in an excess of a 30% solution of hydrogen bromide and treated in a manner identical to that described in Example 13A) (a) to give 2-amino-N-(2-benzoyl-4-chlorophenyl)-N-methylpropionamide hydrobromide as an almost colourless hygroscopic powder of melting point 140°–145° C (slow decomposition) (from acetone/diethyl ether); $[\alpha]_D^{20} = +13.2°$ (c = 1 in ethanol).

Analysis for $C_{17}H_{18}ClN_2O_2$ (397.70): Calculated: C: 51.34; H: 4.56; N: 7.05; Br ion: 20.10. Found: C: 50.98; H: 4.73; N: 6.78; Br ion: 20.05; H$_2$O: 0.75.

Water-free: C: 51.37; H: 4.68; N: 6.83; Br ion: 20.20.

b. In a manner analogous to that described in Example 13A) (c) there was obtained a mixture of 7-chloro-1,3-dihydro-1,3-dimethyl-5-phenyl-2H-1,4-benzodiazepin-2-one and (N-benzyloxycarbonyl-L-phenylalanyl)-N-(2-benzoyl-4-chlorophenyl)-N-methyl-L-alaninamide in the approximate proportions of 2:1.

B. The process 6.0 g of the mixture obtained according to the preceding paragraph were dissolved in 40 ml of a 30% solution of hydrogen bromide in glacial acetic acid and the solution was stirred at room temperature for 3 hours. The mixture was worked up in a manner analogous to that described in Example 13B) (i) to give 0.6 g of L-phenylalanyl-N-(2-benzoyl-4-chlorophenyl)-N-methyl-L-alaninamide as an almost colourless light-sensitive brittle foam; $[\alpha]_D^{20} = -34.9°$ (c = 1 in ethanol).

Analysis for $C_{26}H_{26}ClN_3O_3$ (463.97): Calculated: C: 67.30; H: 5.65; N: 9.06; Cl: 7.64. Found: C: 66.98; H: 5.79; N: 8.82; Cl: 7.74.

The foregoing free base was converted into the hydrochloride as follows:

0.5 g of L-phenylalanyl-N-(2-benzoyl-4-chlorophenyl)-N-methyl-L-alaninamide was dissolved in a minimum amount of methanol at room temperature and treated, by titration, with an exact equivalent of 1-N hydrochloric acid. The solvent was removed from the resulting solution by evaporation in vacuo at room temperature and finally by lyophilisation to give, in quantitative yield, L-phenylalanyl-N-(2-benzoyl-4-chlorophenyl)-N-methyl-L-alaninamide hydrochloride as a white hygroscopic light-sensitive amorphous powder of melting point 130°–140° C (slow decomposition); $[\alpha]_D^{20} = -40.0°$ (c = 1 in water).

Analysis for $C_{26}H_{27}Cl_2N_3O_3$ (500.43): Calculated: C: 62.39; H: 5.44; N: 8.40; Cl ion: 7.09. Found: C: 60.84; H: 5.65; N: 8.03; Cl ion: 7.36; H$_2$O: 2.05.

Water-free: C0 62.11; H: 5.53; N: 8.20; Cl ion: 7.51.

Calculated for $C_{26}H_{26}ClN_3O_3$. 1.05 HCl (502.28): C: 62.17; H: 5.42; N: 8.36; Cl ion: 7.41.

EXAMPLE 23

A. The preparation of the starting material a. In a manner analogous to that described in Example 13A) there was obtained 2-(N-benzyloxycarbonylamino)-N-(2-benzoylphenyl)-N-methylacetamide as a pale yellow gum.

Analysis for $C_{24}H_{22}N_2O_4$ (402.45): Calculated: C: 71.63; H: 5.51; N: 6.96. Found: C: 71.33; H: 5.45; N: 6.90.

b. Treatment of the compound obtained according to the preceding paragraph in a manner analogous to that described in Example 13A) gave L-alanyl-N-(2-benzoylphenyl)-N-methylglycinamide as an almost colourless light-sensitive foam.

Analysis for $C_{19}H_{21}N_3O_3$ (339.40): Calculated: C: 67.24; H: 6.24; N: 12.38. Found: C: 66.93; H: 6.01; N: 11.98.

In addition, 1,3-dihydro-1-methyl-5-phenyl-2H-1,4-benzodiazepin-2-one of melting point 151°–154° C was isolated as a major by-product.

B. The process 3 g of L-alanyl-N-(2-benzoylphenyl)-N-methylglycinamide were dissolved in 10 ml of anhydrous sulphuric acid at room temperature. The resulting mixture was cooled to −5° C and treated dropwise by the addition of a solution of 0.94 g of potassium nitrate in 3 ml of anhydrous sulphuric acid. The resulting mixture was stirred at 0° C for 10 hours and finally allowed to warm to room temperature overnight. The mixture was then poured into an excess of ice-water. The pH of the mixture was adjusted to approximately pH 9 by the addition of concentrated ammonium hydroxide, care being taken to maintain the temperature at ca 0° C. The mixture obtained was extracted with several portions of dichloromethane. The combined organic phases were washed successively with 2-N sodium carbonate solution and water, dried over anhydrous magnesium sulphate and evaporated in vacuo. The residue (ca 3 g) was dissolved in a minimum amount of chloroform and subjected to column chromatography on Florisil using mixtures of methanol in chloroform in increasing proportions. Fractions were collected using 5% (vol/vol) methanol in chloroform and evaporated in vacuo to give 1.75 g (52%) of pure L-alanyl-N-(2-benzoyl-4-nitrophenyl)-N-methylglycinamide as an almost colourless light-sensitive foam; $[\alpha]_D^{20} = +2.1°$ (c = 1 in ethanol).

Analysis for $C_{19}H_{20}N_4O_5$ (384.40): Calculated: C: 59.37; H: 5.25; N: 14.57. Found: C: 59.94; H: 5.43; N: 14.17.

The foregoing free base was dissolved in a minimum amount of methanol at room temperature and treated, by titration, with an exact equivalent of 1-N hydrochloric acid. The solution was removed from the resulting solution by evaporation in vacuo at room temperature and finally by lyophilisation to give, in quantitative yield, L-alanyl-N-(2-benzoyl-4-nitrophenyl)-N-methylglycinamide hydrochloride as a white amorphous solid of melting point 165°–175° C (slow decomposition): $[\alpha]_D^{20} = +7.5°$ (c = 1 in water).

Analysis for $C_{19}H_{21}ClN_4O_5$ (420.85): Calculated: C: 54.23; H: 5.03; N: 13.31; Cl ion: 8.42. Found: C: 54.12; H: 5.30; N: 13.05; Cl ion: 8.42.

EXAMPLE 24

A. The preparation of the starting material:

i. 2.0 g of 8-chloro-1-methyl-6-phenyl-4H-s-triazolo-[4.3-a] [1,4]benzodiazepine [J. B. Hester Jr., A. D. Rudzic and B. V. Kamdar, J. Med. Chem., 1971, 14, 1078] were dissolved in 40 ml of dilute hydrochloric acid and left at room temperature overnight. The solution was evaporated to an oil which was dissolved in water and re-evaporated. The final traces of water were removed by shaking the oil with 50% methanol/toluene followed by evaporation. This treatment was repeated three times with 50% methanol/toluene and twice with toluene. This gave 5-chloro-2-(3-aminomethyl-5-methyl-4H-1,2,4-triazol-4-yl)benzophenone hydrochloride as a foam.

ii. The foam prepared as described in the preceding paragraph was dissolved in 25 ml of dry dimethylformamide and to the resulting solution were added 2.64 g of N-benzyloxycarbonyl-L-phenylalanine N-hydroxysuccinimide ester. The solution obtained was then cooled to $-20°$ C. A solution of 2.1 ml of N-ethylmorpholine in 8.4 ml of dimethylformamide was added to the vigorously stirred solution over a period of 0.5 hour. The resulting mixture was stirred for 1 hour at $-20°$ C and left overnight at room temperature. The solvent was removed in vacuo and the residue was dissolved in a mixture of dichloromethane and water. The layers were separated and the aqueous layer was extracted with additional dichloromethane. The organic solutions were combined, washed five times with water, dried over magnesium sulphate and evaporated to an oil which was chromatographed on silica gel. Elution was carried out initially using chloroform and then using 2% methanol in chloroform, 15 ml fractions being collected. Fractions 1-25 comprised the chloroform eluate and the product was contained in fractions 48-57. These latter fractions were combined, evaporated to dryness and the residue crystallised from ethyl acetate/petroleum ether. 1.8 g (45%) of 5-chloro-2-[[(N-benzyloxycarbonyl-L-phenylalanyl)aminomethyl]-5-methyl-4H-1,2,4-triazol-4-yl]benzophenone of melting point 84°-88° C were obtained.

B. The process 0.50 g of 5-chloro-2-[[N-benzyloxycarbonyl-L-phenylalanyl)aminomethyl]-5-methyl-4H-1,2,4-triazol-4-yl]benzophenone was treated with a 35% solution of hydrogen bromide in glacial acetic acid for 1 hour. Dry diethyl ether was then added and the separated solid was filtered off, washed with ether and dried in vacuo. The crude product was purified by precipitation from methanol/ethyl acetate. There was obtained 0.36 g (79%) of 5-chloro-2-[3-(L-phenylalanylaminomethyl)-5-methyl-4H-1,2,4-triazol-4-yl]benzophenone dihydrobromide of melting point 164°-171° C (slow decomposition).

Analysis for $C_{26}H_{26}Br_2ClN_5O_2$ (635.79): Calculated: C: 49.12; H: 4.12; N: 11.02; Cl: 5.58; Br: 25.14. Found: C: 48.15; H: 4.14; N: 10.66; Cl: 5.32; Br: 24.52; $H_2O$: 1.83.

Water-free: C: 49.05; H: 4.01; N: 10.86; Cl: 5.42; Br: 24.98.

EXAMPLE 25

In a manner analogous to that described in Example 24, but using $N^a,N^\epsilon$-ditertbutoxycarbonyl-L-lysine N-hydroxysuccinimide ester, there was obtained 5-chloro-2-[3-(L-lysylaminomethyl)-5-methyl-4H-1,2,4-triazol-4-yl]benzophenone trihydrobromide as a lyophilised solid; $[\alpha]_D^{20} = +11.0°$ (c = 1 in water).

Analysis for $C_{23}H_{30}Br_3ClO_2$ (697.71): Calculated: C: 39.60; H: 4.33; N: 12.05; Br: 34.36. Found: C: 38.23; H: 4.38; N: 11.55; Br: 33.40; $H_2O$: 2.58.

Water-free: C: 39.24; H: 4.21; N: 11.86; Br: 34.28.

EXAMPLE 26

In a manner analogous to that described in Example 24, there was obtained 2',5-dichloro-2-[3-(L-phenylalanylamino-methyl)-5-methyl-4H-1,2,4-triazol-4-yl]benzophenone dihydrobromide of melting point 188°-193° C.

Analysis for $C_{26}H_{25}Br_2Cl_2N_5O_2$ (670.25): Calculated: C: 46.59; H: 3.76; N: 10.45; Br: 23.84; Cl: 10.58. Found: C: 46.02; H: 3.83; N: 10.03; Br: 23.33; Cl: 10.35; $H_2O$: 1.90.

Water-free: C: 46.91; H: 3.69; N: 10.22; Br: 23.78; Cl: 10.55.

EXAMPLE 27

In a manner analogous to that described in Example 24, there was obtained 2',5-dichloro-2-[3-(L-lysylaminomethyl)-5-methyl-4H-1,2,4-triazol-4-yl]benzophenone hydrobromide (1:2.9) of melting point 240°-245° C; $[\alpha]_D^{20} = +9.8°$ (c = 1 in water).

Analysis for $C_{23}H_{26}Cl_2N_6O_2$. 2.9 HBr (724.07): Calculated: C: 38.15; H: 4.02; N: 11.61; Br ion: 32.00. Found: C: 37.84; H: 4.13; N: 11.18; Br ion: 31.30; $H_2O$: 1.23.

Water-free: C: 38.31; H: 4.04; N: 11.32; Br ion: 31.69.

EXAMPLE 28

In a manner analgous to that described in Example 24, there was obtained 2',5-dichloro-2-(3-glycylaminomethyl-5-methyl-4H-1,2,4-triazol-4-yl)benzophenone dihydrobromide methanolate of melting point 235°-240° C.

Analysis for $C_{20}H_{23}Br_2Cl_2N_5O_3$ (612.15): Calculated: C: 39.24; H: 3.79; N: 11.44; Br: 26.11; Cl: 11.58. Found: C: 39.39; H: 3.67; N: 11.30; Br: 26.10; Cl: 11.58.

EXAMPLE 29

A. The preparation of the starting material i. A solution of 200 g of 7-chloro-1,3-dihydro-5-(2-fluorophenyl)-2H-1,4-benzodiazepin-2-one in 2 liters of tetrahydrofuran and 250 ml of benzene was saturated with methylamine with cooling in an ice-bath. A solution of 190 g of titanium tetrachloride in 250 ml of benzene was added through a dropping funnel within 15 minutes. After completion of the addition, the mixture was stirred and refluxed for 3 hours. 600 ml of water were added slowly to the cooled mixture. The inorganic material was separated by filtration and was washed well with tetrahydrofuran. The water layer was separated and the organic phase dried over sodium sulphate and evaporated. The crystalline residue was collected to give 7-chloro-5-(2-fluorophenyl)-2-methylamino-3H-1,4-benzodiazepine of melting point 204°-206° C. An analytical sample was recrystallised from methylene chloride/ethanol and had a melting point of 204°-206° C.

ii. 8.63 g of sodium nitrile were added in three portions over a 15 minute to a solution of 30.15 g of 7-chloro-5-(2-fluorophenyl)-2-methylamino-3H-1,4-benzodiazepine in 150 ml of glacial acetic acid. After stirring for 1 hour at room temperature, the mixture was diluted with water and extracted with methylene chloride. The extracts were washed with saturated sodium bicarbonate solution, dried over sodium sulphate and evaporated, at the end azeotropically with toluene to yield 29 g of crude 7-chloro-5-(2-fluorophenyl)-2-(N-nitrosomethylamino)-3H-1,4-benzodiazepine as a yellow oil.

This oil was dissolved in 100 ml of dimethylformamide and added to a mixture of 200 ml of dimethylformamide, 50 ml of nitromethane and 11.1 g of potassium tert.butoxide which had been stirred under nitrogen for 15 minutes. After stirring for 1 hour at room temperature, the mixture was acidified by the addition of glacial acetic acid, diluted with water and extracted with methylene chloride. The extracts were washed with water, dried over sodium sulphate and evaporated. Crystallisation of the residue from diethyl ether yielded 7-chloro-1,3-dihydro-5-(2-fluorophenyl)-2-nitromethylene-2H-1,4-benzodiazepine of melting point 170°–172° C. An analytical sample was recrystallised from methylene chloride/ethanol and had a melting point of 174°–176° C.

iii. A solution of 16.5 g of 7-chloro-1,3-dihydro-5-(2-fluorophenyl)-2-nitromethylene-2H-1,4-benzodiazepine in 500 ml of tetrahydrofuran and 250 ml of methanol was hydrogenated with 5 teaspoonsful of Raney nickel for 2.5 hours at atmospheric pressure. Separation of the catalyst and evaporation left 14 g of crude 2-aminomethyl-7-chloro-2,3-dihydro-5-(2-fluorophenyl)-1H-1,4-benzodiazepine.

iv. 7 ml of acetic anhydride were added to a solution of 6.16 g of crude 2-aminomethyl-7-chloro-2,3-dihydro-5-(2-fluorophenyl)-1H-1,4-benzodiazepine in 200 ml of methylene chloride. The solution was layered with 200 ml of saturated aqueous sodium bicarbonate and the mixture was stirred for 20 minutes. The organic layer was separated, washed with sodium bicarbonate solution, dried over sodium sulphate and evaporated to leave 6.2 g of resinous 2-acetaminomethyl-7-chloro-2,3-dihydro-5-(2-fluorophenyl)-1H-1,4-benzodiazepine.

This material was heated with 40 g of polyphosphoric acid at 150° C for 10 minutes. The cooled mixture was dissolved in water, made alkaline with ammonia and ice and extracted with methylene chloride. The extracts were dried and evaporated and the residue (5.7 g) was chromatographed over 120 g of silica gel using 20% methanol in methylene chloride. The clear fractions were combined and evaporated to yield resinous 8-chloro-3a,4-dihydro-6-(2-fluorophenyl)-1-methyl-4H-imidazo-[1,5-a][1,4]benzodiazepine. A mixture of this material with 500 ml of toluene and 30 g of manganese dioxide was heated to reflux for 1.5 hours. The manganese dioxide was separated by filtration over Celite. The filtrate was evaporated and the residue crystallised from diethyl ether to yield 8-chloro-6-(2-fluorophenyl)-1-methyl-4H-imidazo[1,5-a][1,4]benzodiazepine of melting point 152°–154° C. An analytical sample was recrystallised from methylene chloride/hexane.

b.

i. 2.0 g of 8-chloro-6-(2-fluorophenyl)-1-methyl-4H-imidazo[1,5-a][1,4]benzodiazepine were dissolved in 15 ml of dilute hydrochloric acid and left at room temperature overnight. The solution was evaporated to an oil which was dissolved in water and re-evaporated. The final traces of water were removed by shaking the oil with 50% methanol/toluene followed by evaporation. This treatment was repeated three times with 50% methanol/toluene and twice with toluene. This gave 5-chloro-2'-fluoro-2-(5-aminomethyl-2-methyl-1-imidazolyl)-benzophenone dihydrochloride as a pale yellow solid.

ii. The solid prepared as described in the preceding paragraph was dissolved in 20 ml of dry dimethylformamide and to the resulting solution were added 1.56 g of N-benzyloxycarbonyl-L-leucyl N-hydroxysuccinimide ester. The solution obtained was then cooled to −20° C. A solution of 2.5 ml of N-ethylmorpholine in 10 ml of dimethylformamide was added dropwise with vigorous stirring over a period of 20 minutes. The mixutre was stirred for 1 hour at −20° C and left overnight at room temperature. The solvent was removed in vacuo and the residue dissolved in a mixture of chloroform and water. The layers were separated and the aqueous layer was extracted with additional chloroform. The organic layers were combined, washed five times with water, dried over magnesium sulphate and evaporated to an oil which was chromatographed on 100 g of silica gel. Elution was carried out using 4% methanol in chloroform, 15 ml fractions being collected. The product was eluted in fractions 25–36. These fractions were combined and evaporated to dryness and the resulting oil was crystallised from ether. 1.4 g (43%) of 5-chloro-2'-fluoro-2-[5-[(N-benzyloxycarbonyl-L-leucyl)-aminomethyl]-1-imidazolyl]benzophenone of melting point 63°–75° C (decomposition) were obtained.

Analysis for $C_{32}H_{32}ClFN_4O_4$ (591.09): Calculated: C: 65.02; H: 5.46; N: 9.48. Found: C: 64.66; H: 5.61; N: 9.19.

B. The process 0.40 g of 5-chloro-2'-fluoro-2-[5-[(N-benzyloxycarbonyl-L-leucyl)aminomethyl]-1-imidazolyl]benzophenone was treated with a 35% solution of hydrogen bromide in glacial acetic acid for 45 minutes. Dry diethyl ether was then added, an oily solid being obtained. The product was precipitated from methanol/ethyl acetate, dissolved in water and freeze-dried. There was obtained 5-chloro-2'-fluoro-2-[5-(L-leucylaminomethyl)-2-methyl-1-imidazol]benzohenone dihydrobromide in a yield of 0.25 g (60%); $[\alpha]_D^{20} = -5.5°$ (c = 0.2708 in water).

Analysis for $C_{24}H_{28}Br_2ClFN_4O_2$ (618.77): Calculated: C: 46.59; H: 4.56; N: 9.05; Br: 25.82. Found: C: 44.93; H: 4.74; N: 8.56; Br: 25.04; $H_2O$: 3.55.

Water-free: C: 46.58; H: 4.50; N: 8.87; Br: 25.96.

EXAMPLE 30

In a manner analogous to that described in Example 29, there was obtained 5-chloro-2'-fluoro-5-[(L-alanylaminomethyl)-2-methyl-1-imidazolyl]benzophenone dihydrobromide of melting point 90°–110° C (slow decomposition).

EXAMPLE 31

The following Example illustrates a typical pharmaceutical preparation containing one of the substituted-phenyl ketones provided by this invention.

EXAMPLE A

An injection solution containing the following ingredients is prepared in a conventional manner:

| | |
|---|---|
| L-lysyl-N-(2-benzoyl-4-chlorophenyl)-N-methylglycinamide dihydrochloride | 10.00 mg |
| Sodium acetate 3H$_2$O | 22.32 mg |
| Acetic acid | 2.16 mg |
| Chlorocresol | 1.00 mg |

| -continued | |
|---|---|
| Sodium chloride | q.s. |
| Water for injection ad | 1.00 ml |

The foregoing solution should be protected from light prior to use.

We claim:

1. A compound of the general formula

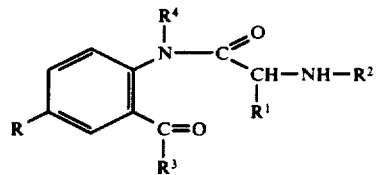

wherein R is selected from the group consisting of a halogen atom, nitro and a trifluoromethyl group; $R^1$ is a hydrogen atom or a lower alkyl group; $R^2$ is an acyl group derived from a naturally occurring amino acid; $R^3$ is a 2-pyridyl group; and $R^4$ is selected from the group consisting of a hydrogen atom, a methyl, cyclopropylmethyl, di($C_{1-4}$alkyl) aminoethyl, methoxymethyl and a hydroxyethyl group or the acid addition salts thereof.

* * * * *